United States Patent [19]

Scheller

[11] Patent Number: 4,634,589

[45] Date of Patent: Jan. 6, 1987

[54] DENTIFRICE FOR HYPERSENSITIVE TEETH

[75] Inventor: Hans-Ulrich Scheller, Eislingen, Fed. Rep. of Germany

[73] Assignee: Wurttembergische Parfumerie-Fabrik GmbH, Eislingen, Fed. Rep. of Germany

[21] Appl. No.: 731,286

[22] Filed: May 7, 1985

[30] Foreign Application Priority Data

May 18, 1984 [DE] Fed. Rep. of Germany ....... 3418427

[51] Int. Cl.$^4$ ........................... A61K 7/16; A61K 7/18
[52] U.S. Cl. ........................................ 424/49; 424/52; 424/57; 424/151
[58] Field of Search ..................................... 424/49–58

[56] References Cited

U.S. PATENT DOCUMENTS

| | | | |
|---|---|---|---|
| 4,048,300 | 9/1977 | Tomlinson et al. | 424/57 |
| 4,177,258 | 12/1979 | Gaffar et al. | 424/52 |
| 4,183,915 | 1/1980 | Gaffar et al. | 424/52 |
| 4,327,079 | 4/1982 | Aoki | 424/57 |
| 4,342,741 | 8/1982 | Aoki | 424/57 |

FOREIGN PATENT DOCUMENTS 2134862 1/1973 Fed. Rep. of Germany .

OTHER PUBLICATIONS

Koedderman and Scheller, C.A., 78, #128425v (1973) of Ser. Offen. 2134862, Jan. 25, 1973.
Kosti, C.A., 82, #144949g (1975) of U.S. Pat. No. 3,832,460, Aug. 27, 1974.

Primary Examiner—Shep K. Rose

[57] ABSTRACT

A dentifrice for hypersensitive teeth containing at least 15% by weight of an apatite having an average particle size of less than 8 μm and an abrasion value (RDA) of less than 30 as the sole crystalline and polishing substance. No further soluble mineral salts are present in the dentifrice. The dentifrice may also contain a local anesthetic.

2 Claims, No Drawings

DENTIFRICE FOR HYPERSENSITIVE TEETH

BACKGROUND OF THE INVENTION

The present invention relates to a dentifrice for hypersensitive teeth containing an apatite having an average particle size of less than 10 μm and, optionally, a local anesthetic.

DESCRIPTION OF THE PRIOR ART

German Patent Specification No. 21 34 862 describes dentifrices for hypersensitive teeth. However, the dentifrice recipes additionally contained an osmotically effective salt combination comprising sodium hydrogencarbonate, sodium chloride, magnesium carbonate, magnesium chloride, potassium sulfate, etc.

U.S. Pat. No. 3,122,483 discloses adding strontium chloride to dentifrices, since this substance is believed to influence the stimulus conduction in the pulp. From the view of dental medicine influencing the pulp is hardly desired and may involve other negative consequences.

A further means for treating hypersensitivities is by local application of amine fluoride solutions. However, this treatment has the drawback of that it can only be carried out in the dentist's office and, with conventional dental care, will only last for a short time.

EVENTS LEADING UP TO THE PRESENT INVENTION

Extensive experimental work directed to improving the commercial product described in the German Patent Specification No. 21 34 862 has led to the surprising result that the addition of strontium chloride did not improve the effect. Rather, it was found that the efficacy could be improved to a significant extent by omitting all soluble mineral salts and employing an apatite having an average particle size of less than 8 μm as the sole crystalline and polishing substance. Moreover, such an apatite has a substantially lower abrasion value (measured as RDA; cf. Radioactive Dentine Abrasion, J. J. Hefferren, J. Dental Research 55, No. 4,563–573 (1976)) of less than 30. The amount of the apatite used must be higher than that of the commercial product, namely at least 15% by weight instead of 9% as used in commercial products to date.

These results were not foreseeable and also cannot be readily interpreted afterwards either. However, the findings suggest that there is some polishing effect. Namely, in the course of polishing there is always formed a continuous vitreous glossy layer at the tooth surface, which layer consists of the base substance of the polished material, on the one hand, and of the polishing agent, on the other hand. In the polishing procedure these two (the base substance and the polishing agent) are closely mechanically attached to each other and fused. Thus, the polishing agent is mechanically rubbed in between the microscopic microcrystalline to atomic unevennesses and roughnesses of the surface and fused with same due to local overheating and formation of an eutectic mixture. If this concept is transferred to the tooth surface, then this could mean that by treatment with large amounts of the finely-divided apatite, the latter is pressed into the exposed small dentin channels. Since the material is the same as that of the hard substance of the tooth, the existing damages can heal if no interfering alien minerals will inhibit the fusion process. Furthermore, the amount of offered apatite must be large enough, and care must be taken to prevent the polished surface being torn open again and destroyed by other abrasive materials.

Further investigations have shown that an increased remineralization occurs, more specifically so with particle sizes of the apatite of less than 4 μm. After 20 applications in vitro, there was already observed a reduction in diameter of the dentin channels by about 50%.

Independently of this subsequent theoretical explanation, it has been established that the desired effect is obtained only if all of the conditions according to the present invention have been fulfilled.

SUMMARY OF THE INVENTION

Thus, it is the object of the present invention to provide a dentifrice for hypersensitive teeth containing an apatite having an average particle size of less than 10 μm and optionally a loal anesthetic, which dentifrice is characterized in that it contains an amount at least 15% by weight of an apatite having an average particle size of less than 8 μm and an abrasion value (RDA) of less than 30 as the sole crystalline and polishing substance, no further soluble mineral salts being present.

DETAILED DESCRIPTION OF THE INVENTION

The apatite to be used in the present invention may be hydroxylapatite, fluoroapatite, or a mixture thereof. It is essential that the amount, particle size, and abrasion value will be observed and maintained and that no other soluble mineral salts can exert any interfering effect.

Silicic acid has been proven to be a non-interfering substance which can be added in an amount of up to 10% by weight without adversely affecting the efficacy of the dentifrice.

The dentifrices according to the present invention of course may additionally contain a local anesthetic such as benzocain, p-aminobenzoic acid ethylester. In addition to glycerol and water, the dentifrices according to the present invention further contain wetting and foaming agents, flavoring agents, and aroma ingredients. If desired, any other additive may be used as long as it is not a soluble mineral salt.

The apatite used in the present invention and having an average particle size of less than 8 μm and an abrasion value (RDA) of less than 30 is known in the art as so-called amorphous hydroxylapatite, fluoroapatite or a mixture thereof. The bulk density of the apatite is preferably less than 180 g/l and mostly in the range of around 150 g/l.

The dentifrice according to the present invention is further illustrted by the following Example and Comparative Examples and Abrasion Tests.

EXAMPLE

| Tooth-paste (Recipe A) | |
| --- | --- |
| Amorphous silicic acid Aerosil 200 | 2.40% |
| Carboxymethylcellulose | 1.00% |
| Sodium laurylsulfate | 2.75% |
| Glycerol (99%) | 20.80% |
| Wetting agent (Hostapon KTW) | 0.90% |
| p-Hydroxybenzoic acid methylester-Na | 0.20% |
| Saccharin—Na | 0.25% |
| Tricalcium hydroxylapatite | 17.00% |
| Water | 50.699% |
| S—Erythrosin 76 E 127 | 0.001% |
| Aroma | 1.50% |

| -continued |
| --- |
| Tooth-paste (Recipe A) |

| | |
| --- | --- |
| Propylene glycol | 2.50% |

The tooth-paste consisting of the above components was subjected to the abrasion test (RDA). The abrasion value was found to be 24.

Clinical examinations of this tooth-paste showed a significant improvement already after 3 to 8 days, and all of the users were found to be pain-free after 15 days at the latest.

COMPARATIVE EXAMPLES

For comparison, the formulations according to the recipes B through G as set forth in the following Table were prepared.

TABLE

| | B | C | D | E | F | G |
| --- | --- | --- | --- | --- | --- | --- |
| Amorphous silicic acid Aerosil 200 | 3.00 | 2.85 | 10.00 | 3.00 | 2.40 | 2.40 |
| Carboxymethylcellulose | 1.00 | 1.00 | 1.00 | 1.00 | 1.00 | 1.00 |
| Sodium larylsulfate | 2.75 | 2.75 | 2.75 | 2.75 | 2.75 | 2.75 |
| Glycerol (99%) | 20.80 | 20.80 | 20.80 | 20.80 | 20.80 | 20.80 |
| Wetting agent (Hostapon KTW) | 0.90 | 0.90 | 0.90 | 0.90 | 0.90 | 0.90 |
| p-Hydroxybenzoic acid methylester-Na | 0.20 | 0.20 | 0.20 | 0.20 | 0.20 | 0.20 |
| Saccharin—Na | 0.25 | 0.25 | 0.25 | 0.25 | 0.25 | 0.25 |
| Tricalcium hydroxylapatite | — | — | — | 9.00 | 17.00 | 17.00 |
| Water | 49.499 | 49.499 | 60.99 | 49.499 | 49.699 | 44.699 |
| S—Erythrosin 76 E 127 | 0.001 | 0.001 | 0.001 | 0.001 | 0.001 | 0.001 |
| Aroma | 1.50 | 1.50 | 1.50 | 1.50 | 1.50 | 1.50 |
| Propylene glycol | 2.50 | 2.375 | 2.50 | 2.375 | 2.50 | 2.50 |
| Potassium sulfate | 0.175 | — | — | 0.175 | — | — |
| Magnesium carbonate | 1.25 | — | — | 1.25 | — | — |
| Sodium hydrogencarbonate | 6.25 | — | — | 6.25 | — | — |
| Sodium chloride | 0.175 | — | — | 0.175 | — | — |
| Titanium dioxide | 0.75 | 0.75 | — | 0.75 | — | — |
| Dicalcium phosphate × 2 H$_2$O | 9.00 | 17.00 | — | — | — | — |
| Benzocain | — | 0.125 | — | 0.125 | — | — |
| Strontium chloride × 6 H$_2$O | — | — | — | — | 6.00 | 5.00 |
| Cetylamine hydrogenfluoride | — | — | — | — | — | 1.00 |

Recipe E conforms to that of the commercial product of German Patent Specification No. 21 34 862. Recipe B conforms to that of the commercial product of Recipe E; however, Recipe B does not contain hydroxyl apatite. Recipe C conforms to Recipe B, but contains benzocain added thereto. Recipe D is a placebo containing no active ingredient at all. Recipes F and G conform to Recipe A according to the invention; however they additionally contain strontium chloride×6H$_2$O or cetylamine hydrogenfluoride, respectively.

As a result of the clinical examination, Recipe A (a dentifrice according to the present invention) was found to be substantially more efficient than the commercial product and some other recipes, although the latter were superior to the placebo.

ABRASION TESTS

The abrasion values (RDA) were determined of the materials according to Recipes A and F and of some known commercial products. It was determined that the abrasion value of Recipe F was already 61. The respective values for the commercial products Blend-a-med, Lacalut, Theramed and Causamed were between 85 and 95.

What is claimed is:

1. In a method of polishing hypersensitive teeth the improvement, showing a significant amelioration after 3 to 8 days, and in which users are found to be pain-free after 15 days wherein there is rubbed or mechanically pressed into the exposed small dentine channels for 3 to 15 days finely divided apatite by application of a dentifrice containing at least 15% by weight of an apatite selected from the group consisting of amorphous hydroxyl apatite, fluoro apatite, and mixtures thereof, having a bulk density of less than 180 g/l having an average particle size of 8 millimicrons and an abrasion value (RDA) of less than 30 as the sole crystalline and polishing substance, said dentifrice containing no further soluble mineral salts.

2. Method of claim 1, wherein the dentifrice has average particle size of less than 4 μm.

* * * * *

UNITED STATES PATENT AND TRADEMARK OFFICE
CERTIFICATE OF CORRECTION

PATENT NO. : 4,634,589

DATED : January 6, 1987

INVENTOR(S) : Dr. Hans-Ulrich SCHELLER

It is certified that error appears in the above-identified patent and that said Letters Patent is hereby corrected as shown below:

Column 4, line 46, before "8" insert --less than--.

Signed and Sealed this

Third Day of January, 1989

Attest:

DONALD J. QUIGG

*Attesting Officer*  *Commissioner of Patents and Trademarks*